(12) United States Patent
Vasilenko

(10) Patent No.: US 10,959,448 B2
(45) Date of Patent: Mar. 30, 2021

(54) METHOD AND DEVICE FOR DISINFECTION AND/OR PURIFICATION OF A PRODUCT

(71) Applicant: Vitabeam Ltd, London (GB)

(72) Inventor: Vladimir Vasilenko, Martintown (CA)

(73) Assignee: Vitabeam Ltd, London (GB)

( * ) Notice: Subject to any disclaimer, the term of this patent is extended or adjusted under 35 U.S.C. 154(b) by 0 days.

(21) Appl. No.: 16/150,548

(22) Filed: Oct. 3, 2018

(65) Prior Publication Data

US 2019/0029293 A1   Jan. 31, 2019

Related U.S. Application Data

(63) Continuation-in-part of application No. 15/267,336, filed on Sep. 16, 2016, now Pat. No. 10,201,172, which is a continuation of application No. 14/617,981, filed on Feb. 10, 2015, now Pat. No. 9,457,109, which is a continuation of application No.
(Continued)

(30) Foreign Application Priority Data

Apr. 21, 2009  (NL) .................................... 1036892

(51) Int. Cl.
| | | |
|---|---|---|
| *A23L 3/26* | (2006.01) |
| *A23B 7/015* | (2006.01) |
| *A61L 2/08* | (2006.01) |
| *A01G 7/00* | (2006.01) |
| *A61L 9/18* | (2006.01) |
| *A23B 4/015* | (2006.01) |
| *C02F 1/30* | (2006.01) |
| *A61L 2/00* | (2006.01) |
| *A23B 5/015* | (2006.01) |

(52) U.S. Cl.
CPC ................ *A23L 3/26* (2013.01); *A23B 4/015* (2013.01); *A23B 5/015* (2013.01); *A23B 7/015* (2013.01); *A61L 2/0058* (2013.01); *A61L 2/085* (2013.01); *A61L 9/18* (2013.01); *C02F 1/30* (2013.01); *A23V 2002/00* (2013.01); *A61L 2/084* (2013.01); *A61L 2202/11* (2013.01); *C02F 2303/04* (2013.01)

(58) Field of Classification Search
CPC ....................................................... A61L 2/085
USPC ............................................................ 422/22
See application file for complete search history.

(56) References Cited

U.S. PATENT DOCUMENTS

2003/0009933 A1 *   1/2003   Yoneda .................. A01G 7/045
                                                        47/1.01 R

FOREIGN PATENT DOCUMENTS

| GB | 2303533 A | * | 2/1997 | ............... A01C 1/00 |
| WO | WO-2004100684 A1 | * | 11/2004 | ............... A01N 3/00 |

OTHER PUBLICATIONS

Takahashi et al., Photosynthesis modulates the sign of phototaxis of wild-type Chlamydomonas reinhardtii, Dec. 1993, FEBS Letters, vol. 336 Issue 3, pp. 516-5620 (Year: 1993).*

(Continued)

*Primary Examiner* — Holly Kipouros
(74) *Attorney, Agent, or Firm* — Berggren LLP

(57) ABSTRACT

This invention provides a method and device for disinfecting any products, materials or environment as any complex of physical, chemical, and biotic factors that can include gases, liquids and solids like soil or artificial plant growing media or animals and plants comprising the step of treating them with one or more infrared lights of LED emitters.

11 Claims, 3 Drawing Sheets

Related U.S. Application Data

13/265,650, filed as application No. PCT/EP2010/055276 on Apr. 21, 2010, now abandoned.

(56) References Cited

OTHER PUBLICATIONS

Johnson et al., Infrared light-emitting diode radiation causes gravitropic and morphological effects in dark-grown oat seedlings, 1996, Photochemistry and Photobiology, 63(2) pp. 238-242 (Year: 1996).*

* cited by examiner

US 10,959,448 B2

METHOD AND DEVICE FOR DISINFECTION AND/OR PURIFICATION OF A PRODUCT

PRIORITY

This is a continuation-in-part application of U.S. patent application Ser. No. 15/267,336 filed on Sep. 16, 2016 and claiming priority of U.S. patent application Ser. No. 14/617,981 filed on Feb. 20, 2015 and issued on Apr. 10, 2016 as, U.S. Pat. No. 9,457,109, claiming priority of U.S. patent application Ser. No. 13/265,650 filed on Dec. 20, 2010 being U.S. national entry of PCT/EP2010/055276, filed on Apr. 21, 2010 and claiming priority of NL patent application 1036892, the contents of all which are incorporated herein by reference.

FIELD OF THE INVENTION

The present invention relates to method and device for purification or disinfection of products using infrared light. In particular, it relates to the purification or disinfection of fresh produce, living organisms, liquids, air and solids using infrared light.

BACKGROUND OF THE INVENTION

Purification methods using light, in particular UV light are known and accepted in industrial application for a long time. For example, in sewage stations it is known to purify spoiled water using UV light in the form of long tubes, e.g. included in racks that are lowered in a water stream for longitudinal passage of water. Another application for "exterior disinfecting" of produce products is known from patent publication U.S. Pat. No. 6,132,784.

Patent publication WO2005031881 indicates disinfecting such as for water purification may also be performed by LED lamps, the advantage being "an appreciably superior effectiveness" over "disinfecting lamps known today—2004—(TUV, HOK and DBD)". This invention uses UV light.

Other types of disinfecting lamps are recently proposed through the use of infrared or near infrared light. One example, from U.S. Pat. No. 6,030,653, discloses the use of visible and infrared light for cold pasteurization a food product. The visible light illumination always has to be preceded by illumination with near infrared light to create 'an optical window'. A method and device using LED for purification of water are known. Use of infrared light for water purification purposes is known as being a relatively low-cost purification method. However, the known art requires further technical development. It is therefore an object of the present invention to arrive to a generally applicable, highly effective method using LED components in a functional and economic manner, preferably in a manner applicable both in water purification as well as in living tissue products like fresh produce, flowers, fish and the like.

DETAILED DESCRIPTION OF THE INVENTION

The present invention relates to a method for disinfecting or purifying a product. The method comprises illuminating a product with infrared light from one or more light emitting diodes.

One advantage of the present invention is that products are illuminated and purified or disinfected at the same time. This is important at various locations, such as for example at retail shops for improved illumination of flowers and fresh produce which is presented for sale. Using the method or device according to the present invention, such display for sale is improved in quality because the colors of the product are reflected correctly, and the shelf-life and freshness of the product is extended by the external and internal disinfection or purification.

A concomitant advantage is that freshness of products may be maintained at the work station, while maintaining and even improving the human vision at the work station in a safe way. This could not be achieved using UV light, which is damaging to the human eye. Yet another advantage is that using the method or device of the present invention, freshness may be maintained longer, not only in a conditioned environment, e.g. under cooled circumstances, but also outside a conditioned environment, due to the sanitary and respiratory impulse of elimination according to the present invention.

In the present context, the terms 'LED', 'LED element' and 'light emitting diode' are used interchangeably and refer to light emitting diodes in all known forms, be it inorganic, organic, point-like, line-like. In one embodiment, the LEDs are wide angle elements, which refers to LEDs which deliver nicely spread light rather than spotlights. In the present context, the phrase 'purifying or disinfecting a product' refers to the reduction of the number of microorganisms present on or in a product. In the present context, the terms 'infrared light' and 'IR light' are used interchangeably and refer to electromagnetic radiation of a wavelength in the range of about 700 to about 1000 nm. The term 'near infrared light' is used here as well to refer to wavelengths in the range of 700 to about 1000 nm.

In the present context, 'white light' refers to electromagnetic radiation which is visible to the human eye and which has a wavelength within the range of about 380 to about 800 nm. The term 'warm white light' refers to white light with a wavelength within the range of 425 nm to 475 nm, preferably with the peak of emission around 455-465 nm. The term 'cold white light' refers to white light with a wavelength within the range of about 500 nm to about 700 nm, with the peak of emission around 600 nm.

According to the method of the present invention, the product is illuminated by IR light emitted by one or more LED elements. In a preferred embodiment, the IR light emitted by the LED is of a wavelength within a range from 900 nm to 960 nm. Preferably, the light emitted by the IR LED element has a wavelength of 940 nm. According to certain embodiments the emitted IR light has at least one peak within the range of 900-960 nm.

According to the method of the present invention the IR light is emitted by the LED within a range of 800-960 nm with one peak preferably within range of 800 to 890 nm, more preferably within 850 to 890 nm and another peak preferably in a range of 900 to 960.

The intensity of the IR light is preferably between 10-1000 µmol m$^{-2}$s$^{-1}$ In another embodiment according to the invention, the product is illuminated by a combination of IR light and white light. The IR light and white light are typically emitted simultaneously and by separate LEDs. Preferably, the LEDs emitting white light comprise LEDs emitting cold white light and LEDs emitting warm white light. In a preferred embodiment, the product is illuminated by a set of LEDs comprising one or more LEDs emitting IR light of a wavelength within a range from 900 nm to 960 nm, one or more LEDs emitting warm white light with a wavelength within a range of 425 nm to 475 nm and one or more LEDs emitting cold white light with a wavelength within a range of 500 nm to 700 nm. More preferably, the product is illuminated by a set of LEDs comprising one or more LEDs emitting IR light with a wavelength of 940 nm to 950 nm, one or more LEDs emitting warm white light with a wavelength within a range of 455 to 465 nm and one or more LEDs emitting cold white light with a wavelength within a range of 600 to 620 nm. The LEDs may be used in high power output and may emit continuously or may be pulsating. If pulsating emission is used, pulsation is preferably with high frequency. The radiant output of the LEDs is preferably at least 10 mW, more preferably, it is at least 50 mW, at least 100 mW, at least 500 mW or at least 1 W. More preferably, the LEDs are high power LEDs with a radiant output of at least 5 W, at least 10 W, at least 15 W, at least 20 W, at least 25 W, at least 30 W, at least 35 W or at least 40 W, in pulsed or continuous mode. In one embodiment, the LEDs are high power LED elements with a light intensity of at least 500 mW/cm$^2$, at least 600 mW/cm$^2$, at least 700 mW/cm$^2$, at least 800 mW/cm$^2$, at least 900 mW/cm$^2$ or at least 1000 mW/cm$^2$, in pulsed or continuous mode. Preferably, high power LEDs deliver in pulsed mode at least 1.5 W/cm$^2$, at least 2.0 W/cm$^2$, at least 2.5 W/cm$^2$ or at least 3.0 W/cm$^2$. The power output of the LEDs may be adjusted in any convenient way. In one embodiment, the output is adjusted per type of specific wavelength.

The current feeding the LED elements may be continuous or pulsed. Preferably, the feed is pulsed, because this will have a stronger purifying or disinfecting effect. Most preferably, the feed is pulsed with a frequency in the range of 2 Hz to $1\times10^6$ Hz. According to certain embodiments the feed may be pulsed with a frequency of 5 Hz to 100 Hz, with a frequency of 100 Hz-10 kHz, 10 kHz-100 kHz, 100 kHz-500 kHz or 500 kHz-1000 kHz.

Duration of a pulse may be 10 nanoseconds to 10 microseconds.

The duty cycle of pulsation may vary. In one embodiment, the duty cycle of pulsation is 10% duty cycle and 10% power output. In another embodiment, the duty cycle of pulsation is 100%/o duty cycle and 100% power output. Several duty cycles may be combined. Therefore, in one embodiment, the duty cycle in a first setting is 100% duty cycle and 10% power output and in a second setting is 100% duty cycle and 100% power output.

All kinds of bacteria, both Gram positive and Gram negative, fungi, including yeasts, as well as parasites may be combated using the method according to the present invention. Suitable examples include bacteria which belong to the genus *Escherichia, Lactobacillus, Legionella, Leuconostoc, Listeria, Pediococcus, Salmonella, Shigella, Staphylococcus, Vibrio*, or *Yersinia*. Examples of fungi are *Aspergillus, Penicillium*, and *Saccharomyces* Parasite examples are *Cryptosporidium*, and *Giardia*. In particular, the species or isolates referred to as *Escherichia coli, Listeria monocytogens, Salmonella typhi, Shigella dysenteriae, Staphylococcus aureus, Vibrio cholera, Yersinia enterocolitica* and *Giardia lambia*. Also, ESBL-forming bacteria, such as *Escherichia* and *Klebsiella*, may be combated using the method according to the invention.

Without wishing to be bound by theory, the inventor suggests that the method according to the invention is particularly suitable to combat iron dependent bacteria, because it triggers a photoreceptor response mechanism in iron dependent bacteria, such as *E. coli, Salmonella* sp., *Listeria* sp. and *Legionella* sp. This turns off a ferric uptake repressor which prevents aerobactin and specifically enterobactin from being synthesized, thereby inhibiting the assimilation of $FeVFe^{3+}$ by the iron dependent bacterial pathogen, which kills them.

Any product which needs disinfection or purification may be subjected to the method according to the present invention, both organic and inorganic products, both gases, liquids and solids, both metal comprising and metal-free products. Suitable examples of such products include air, water, produce, food, animal products and animals, plant products and plants. Examples of solids and liquids include for example in vitro cultivation media as well as liquid media for growing plants hydroponically. In this disclosure the term animal and plant products are meant to cover any consumable part of a plant or animal. The term animal means alive or a slaughtered animal for consumption. The term animal or animal product includes also edible insects such as crickets for consumption. In addition to edible products such as fruits, vegetables and herbs, eggs, dairy products, grain products, meat and fish, also products such as cut flowers are within the disclosure.

Suitable examples of flowers include flowers such as but not limited to roses, gerberas, tulips, lilies, chrysanthemums, alstroemeria, orchids and gladiolus. Suitable examples of plant products include fruits, such as, citrus fruits, stone fruits, and berries as well as vegetables, sprouts and grains. Non-limiting list of fruits and berries include mangos, avocados, pears, apples, prunes, oranges, strawberries, raspberries, blueberries and bananas. Examples of vegetables include celery, parsley, chives lettuce, herbs, tomatoes, cucumbers, eggplants carrots and potatoes. Non-limiting examples of grain products include maize, rice, wheat, barley, sorghum and oats. The method according to the invention can be used to disinfect plants, their leaves, fruit, flowers and other parts of the plants, e.g. seeds, at any point of the production line, i.e. before or after they are harvested to free them from microorganisms.

The method can be used to disinfect any food product e.g. dairy products, such as milk, cheese and butter; eggs; meat, such as beef, pork, lamb and poultry; fish, such as salmon and tuna as well as lobster, crayfish and other seafood.

The invention is particularly suitable for disinfecting or purifying water sources or containers like sewage, drinking water, swimming pools, whirlpools and all applications where water damp can be inhaled for risk of *Legionella*, such as waste heat water supplies, water distribution networks, cooling towers, showers and Jacuzzi's. The method according to the invention can also be used to disinfect or purify animals, such as the ones which deliver the meat (slaughter house products, poultry) and fish as mentioned above; fruit, flowers and plants before they are harvested to strengthen them and free them from microorganisms; and surfaces, such as from working tables in shops and kitchens. In another aspect, the present invention relates to a device for applying the method according to the present invention in all its embodiments for all the products mentioned above. The device comprises IR LED elements and a power for the LED elements for the purification or disinfection of a product. The IR LED elements are LED elements which emit light within a range from 900 to 960 nm. Preferably, the LED elements are 940 nm LED elements.

In a preferred embodiment, the device further comprises white light LED elements, for use in combination with the IR LED elements. Preferably, the white light LED elements comprise warm white light LED elements and cold white light LED elements. In one embodiment, the white light LED elements comprise a 3000 K LED element. In another embodiment, the white light LED elements comprise a 6500

K LED element. The IR LED elements and the white light LED elements may be arranged in any convenient way. In one embodiment, they are arranged in an alternating manner, i.e. an IR LED element is next to a white light LED element.

The number of IR LED elements and the number of white light LED elements in the device may vary depending on the form of the device and the application for which they are used. In one embodiment, the number of white light LED elements is larger than the number of IR LED elements.

The ratio of warm white light LED elements to cold white light LED elements may also vary depending on the application and the form of the device. In one embodiment, the number of cold white light LED elements is larger than the number of warm white light elements.

The device comprising the LED elements may have any suitable form. In one embodiment, the device has an elongated form and the LED elements are arranged in an elongated panel or string.

The device may be used in a system for purifying or disinfecting a product, as mentioned in the method according to the invention, in all its embodiments and for all the products mentioned above.

Therefore, a system for purification of a product comprising an LED light source for emitting IR light onto the product is also part of the present invention. The IR light source is typically separated from the product. This may be done, for example, by a glass or synthetic material which is transparent for IR light. The LED light source may be included in a holder. In one embodiment, the LED light source is included in an elongated holder for a multiplicity of LED elements.

The product is preferably guided by a guide element. If the holder of the LED source is elongated, the guide element preferably stretches in the direction of elongation of said light source. Holder and guide element may be attached to each other. The guide element may be an elongated tunnel. In one embodiment, the guide element is a tube.

The LED source in the system according to the invention may be positioned in any suitable way. In one embodiment, the LED source is at opposite sides of the guiding element. Preferably, it is at two opposite sides of the guiding element, for example, above and below, or left and right. In one embodiment, the system further comprises a LED light source for emitting white light in combination with the IR light.

The system according to the present invention may be applied in various applications, including all the applications mentioned before for the method. In particular, in refrigerators for professional and domestic use, retail stores, wholesale facilities, slaughter houses, or any food handling facilities, purification of air, swimming pool purification, household application and for purification of shower water. Of more particular interest are applications where water damp can be inhaled for risk of *Legionella*, such as waste heat water supplies, water distribution networks, cooling towers, showers and Jacuzzi's. The method according to the invention can be used to disinfect plants, their leaves, fruit, flowers and other parts of the plants before they are harvested to free them from microorganisms. The plant parts may be plant cuttings for propagation. The plants may also be in vitro plants.

In applications involving a pool of liquid, such as a swimming pool, or tubs as may be used on bathroom shows or flower shows, a bypass system may be provided including a pump for the purpose of letting pass a fraction of the amount of liquid in said pool per unit of time, so as to maintain a proper sanitary level in said pool, in particular to the extent that addition of chemicals like chloric is not at all or to a significantly lowered level required.

EXAMPLES

Example 1

System According to the Invention

Figure 1:
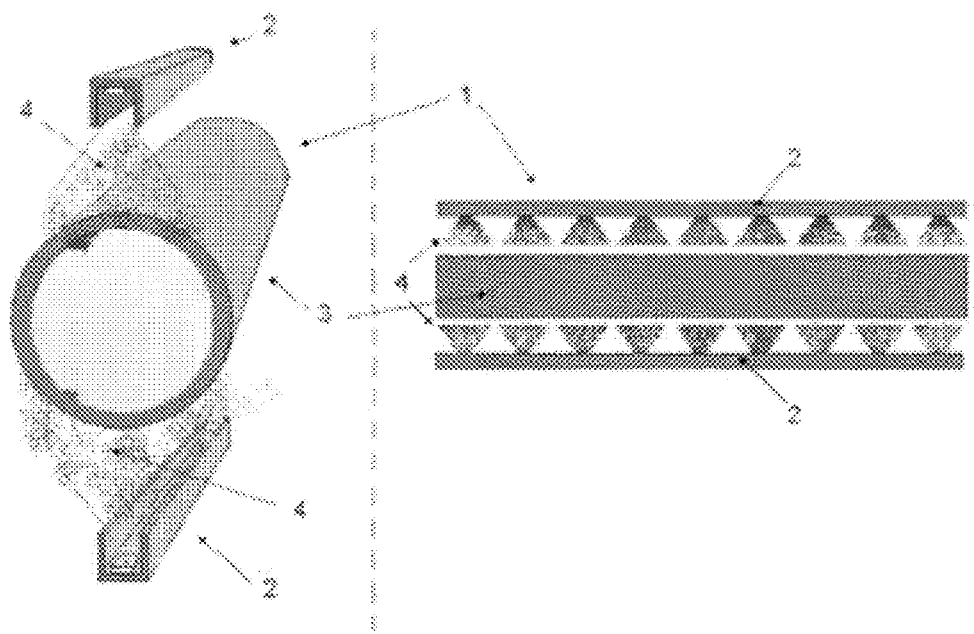
FIG. 1 is an example of a new device applying a new method of IR purification using LED as a light source.

FIG. 1 illustrates a disinfection system (1) in accordance with the present invention. A string of IR and optionally also warm and cold white light LEDs comprised in a casing form a lamp (2). Their radiation (4) illuminates and disinfects the contents of a transparent tube (3). The tube may be a PVC tube, but it may be made of other material as well. A tube is suitable for disinfecting and purifying liquids, e.g. water. Instead of a tube an elongated tunnel may be used for example in case of disinfecting and purifying food products. The string of LED's stretches in the longitudinal direction of the tube over the projected axis of the tube. Two lamps (2) are here included at opposite sides of a tube (3) in the system.

Example 2

Device According to the Invention

Figure 2A:
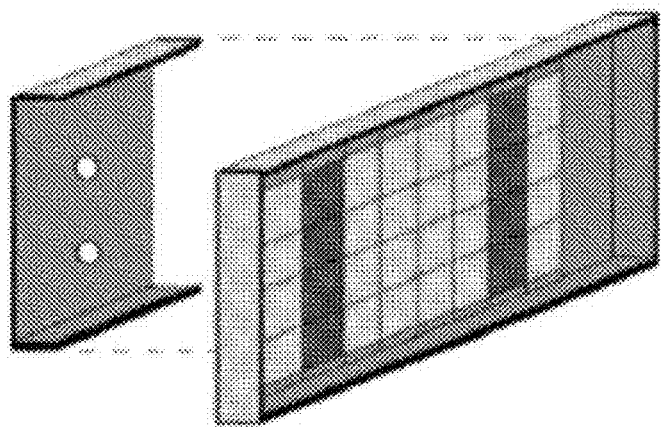
FIG. 2a exemplifies both part of said new device according to FIG. 1, and the new method of applying IR light for the purpose of purification.
Figure 2B:
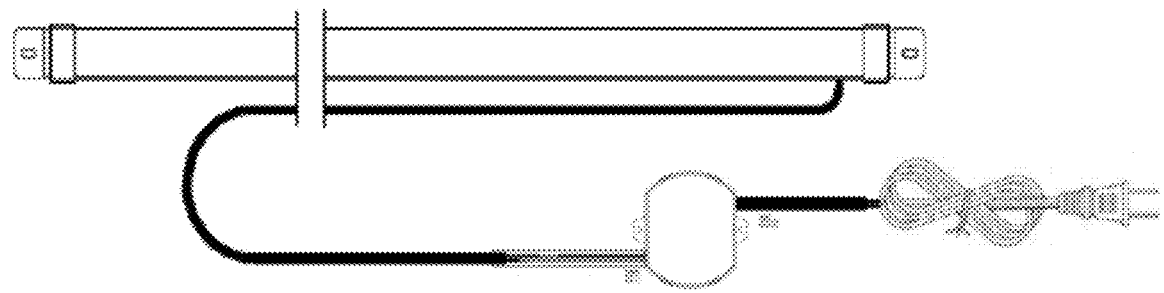
FIG. 2b illustrates an elongated LED light source.

FIG. 2 (a) illustrates a lamp with considerable expansion of the LED's widthwise of the lamp.

This lamp could also be used in the application of FIG. 1, however is typically intended for applications like preserving fresh produce, flowers and the like. It is as well suited for use in sewage stations where the lamp, rather than being immersed in a stream of water, may be hung over such stream, optionally protected by an in between included screen, e.g. of glass or PVC.

The lamp includes IR LEDs separated by white light LEDs. In this example, the IR LEDs are directly flanked by so called cold white light LEDs. The lamp according to the invention may easily be incorporated in existing situations, e.g. for preserving food, in that the height thereof is very limited, in the order of typical measurements of LED, whereas length and width may be dimensioned in accordance with the disinfecting power required for the application. The LEDs panel receive power from an electronic panel which allows to vary the power output of the LED light.

FIG. 2 (b.) The lighting unit consists of an aluminum bar on which is aligned a series of IR LED emitters of at least one peak wavelengths. Its main purpose is to eliminate mold, fungus and bacteria. The light bar allows it to also be installed in areas where space is limited. It may be attached to mounting brackets, which can be adjusted to orient the bar at the required angle and height for the maximum effect during the treatment process.

Example 3

Flower Treatment

Figure 3A:
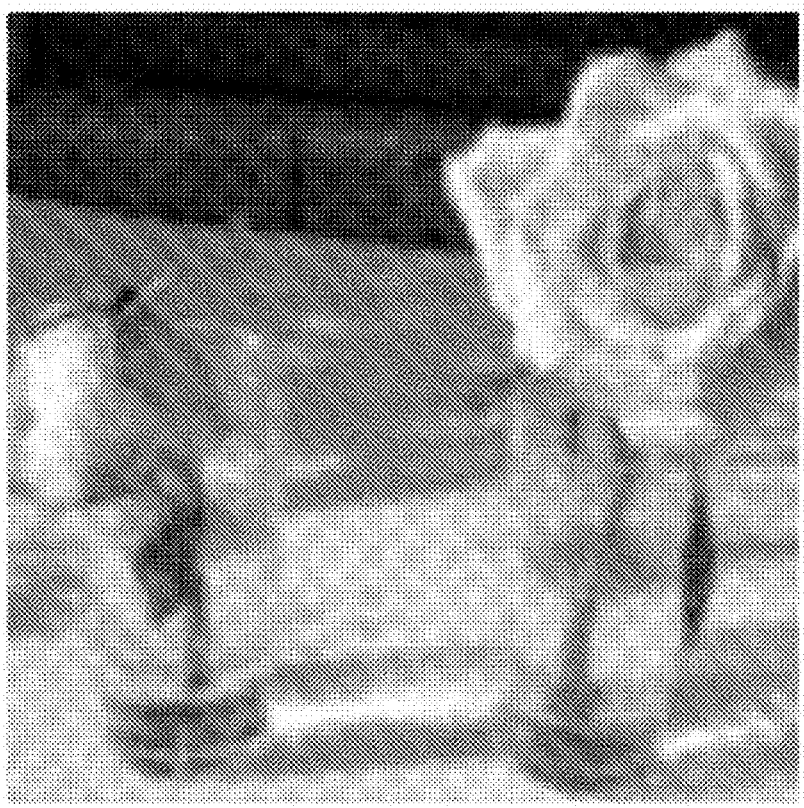
FIG. 3A, B, C shows Gerberas and roses treated according to the method of the invention. Flowers treated according to the method of the invention are on the right and controls are on the left.
Figure 3B:
Figure 3C:

Gerberas and roses were treated according to the method of the invention. They were illuminated 8 hours per day. The illumination was a combination of LEDs emitting IR light (940 nm), cold white light (max 460 nm) and warm white light (max 600 nm). Pulsed light with a pulsation frequency of 600 kHz was used. As a control, gerberas and roses were illuminated with fluorescent light for 8 hours per day. The test continued 24 days. The results are shown in FIG. 3 A-C. Controls are always on the left.

Example 4

Fresh Food Product Treatment

In this example a lighting device providing IR illumination with a peak in the 920 to 960 nm range was installed in a grocery store fresh fish section. The fish was presented on top of ice crush. Control fish was presented in same conditions without the IR illumination. After about 6-8 hours, the ice under the control fish had gained reddish color while the ice under the fish with IR light did not have the color. The fish under the light smelled fresh still after 24 hours while the fish without the light had a 'fishy' smell at the same time point.

Example 5

Treatment of Herbs and Leafy Vegetables

In this example a lighting device providing IR illumination with two peak wavelength areas; one in a range of 850 to 890 nm and another in a range of 900 to 960 nm was used to treat freshly harvested herbs. The plant products were illuminated for 18 hours per day. The material did not show any mold growth after 14 days while the non-treated material was clearly molded after 5 days.

The invention claimed is:

1. A method of reducing the number of bacteria on or in an edible product, said method consisting of the steps of:
   a) providing a device having one or more LED elements, and a power for the one or more LED elements, wherein the one or more LED elements emit infrared light of a wavelength within a range of 800 nm to about 1000 nm, with more than one peak wavelengths, and wherein a radiant output is at least 10 mW; and
   b) illuminating the product with the emitted wavelengths for at least 6-8 hours.

2. The method of claim 1, wherein the infrared light has at least one of the more than one peaks in a range of 900 to 960 nm.

3. The method of claim 1, wherein the infrared light has at least one of the more than one peaks in a range of 900 to 960 nm and at least one of the more than one peaks at 800 to 890 nm.

4. The method of claim 1, wherein said product is a plant product and is selected from the group consisting of vegetable plants, herbs, leafy vegetables, cultivated plants and fruity plants.

5. The method of claim 4, wherein the plant product is illuminated with the emitted wavelengths before harvest.

6. The method of claim 1, wherein the infrared illumination is provided in pulsed manner with a frequency of about 2 Hz to about $1 \times 10^6$ Hz.

7. The method of claim 6, wherein the frequency is in the range of 5 kHz to about 100 kHz.

8. The method of claim 6 wherein duration of a single pulse lasts 10 nanoseconds to 10 microseconds.

9. The method of claim 6, wherein the one or more infrared LED emits light with a power in the range of 1 W to 100 W per a single pulse.

10. The method of claim 1, wherein the infrared illumination is provided in continuous manner.

11. The method of claim 1, wherein the infrared illumination is provided at room temperature or at refrigeration temperature.

* * * * *